United States Patent
Reinhard et al.

(10) Patent No.: US 6,586,244 B2
(45) Date of Patent: Jul. 1, 2003

(54) COMPOSITIONS AND METHODS FOR TREATING NEOPLASTIC DISEASE USING INHIBITORS OF LAMININ5BETA3

(75) Inventors: Christoph J. Reinhard, Alameda, CA (US); Anne B. Jefferson, Oakland, CA (US); Douglas R. Den-Otter, Berkeley, CA (US); Jill A. Winter, Richmond, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/876,176

(22) Filed: Jun. 6, 2001

(65) Prior Publication Data

US 2002/0052334 A1 May 2, 2002

Related U.S. Application Data

(60) Provisional application No. 60/210,409, filed on Jun. 8, 2000.

(51) Int. Cl.[7] .................. C07H 21/04; A61K 48/00; C12N 15/00
(52) U.S. Cl. .............. 435/375; 435/377; 536/23.1; 536/24.5; 536/24.1; 514/44
(58) Field of Search ............... 536/24.1, 24.5, 536/23.1; 530/387.1, 300, 350; 435/375, 377; 514/44

(56) References Cited

PUBLICATIONS

Sudhir Agrawal, TIBTECH, Oct. 1996, vol. 14, pp. 376–387.*
Andrea D. Branch, TIBS 23—Feb., 1998.*
Kuang–Yu Jen et al., Stem Cells 2000; 18: pp. 307–319.*
Bouatrouss et al., "Altered Expression of Laminins in Crohn's Disease Small Intestinal Mucosa," *American Journal of Pathology* 156(1):45–50, Jan. 2000.
Karabulut et al., "Can alterations in integrin and laminin–5 expression be used as markers of malignancy?," *APMIS* 106:1170–1180, 1998.
Koshikawa et al., "Overexpression of Laminin γ2 Chain Monomer in Invading Gastric Carcinoma Cells," *Cancer Research* 59:5596–5601, Nov. 1, 1999.
Lohi et al., "Basement membrane laminin–5 is deposited in colorectal adenomas and carcinomas and serves as a ligand for $\alpha_3\beta_1$ integrin," *APMIS* 108:161–172, 2000.
Salo et al., "Laminin–5 promotes adhesion and migration of epithelial cells: identification of a migration–related element in the γ2 chain gene (LAMC2) with activity in transgenic mice," *Matrix Biology* 18:197–210, 1999.
Skyldberg et al., "Laminin–5 as a Marker of Invasiveness in Cervical Lesions," *Journal of National Cancer Institute* 91(21):1882–1887, Nov. 3, 1999.

* cited by examiner

*Primary Examiner*—Sean McGarry
(74) *Attorney, Agent, or Firm*—Kimberlin L. Morley; Jane E. R. Potter; Robert P. Blackburn

(57) ABSTRACT

Inhibitors of laminin5beta3 are provided that reduce the expression or biological activities of laminin5beta3 or the expression of laminin5beta3 mRNA in a mammalian cell. Laminin5beta3 inhibitors include antisense molecules, ribozymes, antibodies and antibody fragments, proteins and polypeptides as well as small molecules. Laminin5beta3 inhibitors find use in compositions and methods for decreasing laminin5beta3 gene expression as well as methods for inhibiting the proliferation of mammalian cells, including tumor cells of epithelial origin, and methods for treating neoplastic diseases.

9 Claims, 6 Drawing Sheets

Figure 1

```
1     gctttcaggc gatctggaga aagaacggca gaacacacag caaggaaagg tcctttctgg
61    ggatcacccc attggctgaa gatgagacca ttcttcctct tgtgttttgc cctgcctggc
121   ctcctgcatg cccaacaagc ctgctcccgt ggggcctgct atccacctgt tggggacctg
181   cttgttggga ggaccccggtt tctccgagct tcatctacct gtggactgac caagcctgag
241   acctactgca cccagtatgg cgagtggcag atgaaatgct gcaagtgtga ctccaggcag
301   cctcacaact actacagtca ccgagtagag aatgtggctt catcctccgg ccccatgcgc
361   tggtggcagt cccagaatga tgtgaaccct gtctctctgc agctggacct ggacaggaga
421   ttccagcttc aagaagtcat gatggagttc caggggccca tgcccgccgg catgctgatt
481   gagcgctcct cagacttcgg taagacctgg cgagtgtacc agtacctggc tgccgactgc
541   acctccacct tccctcgggt ccgccagggt cggcctcaga gctggcagga tgttcggtgc
601   cagtccctgc ctcagaggcc taatgcacgc ctaaatgggg ggaaggtcca acttaacctt
661   atggatttag tgtctgggat tccagcaact caaagtcaaa aaattcaaga ggtggggag
721   atcacaaact tgagagtcaa tttcaccagg ctggcccctg tgccccaaag gggctaccac
781   cctcccagcg cctactatgc tgtgtccag ctccgtctgc agggagctg cttctgtcac
841   ggccatgctg atcgctgcgc acccaagcct ggggcctctg caggccctc caccgctgtg
901   caggtccacg atgtctgtgt ctgccagcac aacactgccg cccaaattg tgagcgctgt
961   gcacccttct acaacaaccg gccctggaga ccggcggagg gccaggacgc ccatgaatgc
1021  caaaggtgcg actgcaatgg gcactcagag acatgtcact ttgaccccgc tgtgtttgcc
1081  gccagccagg gggcatatgg aggtgtgtgt gacaattgcc gggaccacac cgaaggcaag
1141  aactgtgagc ggtgtcagct gcactatttc cggaaccggc cccgggagc ttccattcag
1201  gagacctgca tctcctgcga gtgtgatccg gatggggcag tgccaggggc tccctgtgac
1261  ccagtgaccg ggcagtgtgt gtgcaaggag catgtgcagg gagagcgctg tgacctatgc
1321  aagccgggct tcactggact cacctacgcc aacccgcagg gctgccaccg ctgtgactgc
1381  aacatcctgg ggtccggag ggacatgccg tgtgacgagg agagtgggcg ctgcctttgt
1441  ctgcccaacg tggtgggtcc caaatgtgac cagtgtgctc cctaccactg gaagctggcc
1501  agtggccagg gctgtgaacc gtgtgcctgc gacccgcaca actcccctca gcccacagtg
1561  caaccagttc acagggcagt gccctgtcgg gaaggctttg gtggcctgat gtgcagcgct
1621  gcagccatcc gccagtgtcc agaccggacc tatggagacg tggccacagg atgccgagcc
1681  tgtgactgtg atttccgggg aacagagggc ccgggctgcg acaaggcatc aggccgctgc
1741  ctctgccgcc ctggcttgac cgggccccgc tgtgaccagt gccagcgagg ctactgcaat
1801  cgctacccgg tgtgcgtggc ctgccaccct tgcttccaga cctatgatgc ggacctccgg
1861  gagcaggccc tgcgctttgg tagactccgc aatgccaccg ccagcctgtg gtcagggcct
1921  gggctggagg accgtggcct ggcctccgg atcctagatg caaagagtaa gattgagcag
1981  atccgagcag ttctcagcag cccgcagtc acagagcagg aggtggctca ggtggccagt
2041  gccatcctct ccctcaggcg aactctccag ggcctgcagc tggatctgcc cctggaggag
2101  gagacgttgt cccttccgag agacctggag agtcttgaca gaagcttcaa tggtctcctt
2161  actatgtatc agaggaagag ggagcagttt gaaaaaataa gcagtgctga tccttcagga
2221  gccttccgga tgctgagcac agcctacgag cagtcagccc aggctgctca gcaggtctcc
2281  gacagctcgc gccttttgga ccagctcagg gacagccgga gagaggcaga gaggctggtg
2341  cggcaggcgg gaggaggagg aggcaccggc agcccaagc ttgtggccct gaggctggag
2401  atgtcttcgt tgcctgacct gacacccacc ttcaacaagc tctgtggcaa ctccaggcag
2461  atggcttgca cccccaatatc atgcctggt gagctatgtc cccagacaa tggcacagcc
2521  tgtggctccc gctgcagggg tgtccttccc agggccggtg ggccttctt gatggcgggg
2581  caggtggctg agcagctgcg gggcttcaat gccagctcc agcggaccag gcagatgatt
2641  agggcagccg aggaatctgc ctcacagatt caatccagtg cccagcgctt ggagacccag
```

Figure 1 (continued)

```
2701 gtgagcgcca gccgctccca gatggaggaa gatgtcagac gcacacggct cctaatccag
2761 caggtccggg acttcctaac agaccccgac actgatgcag ccactatcca ggaggtcagc
2821 gaggccgtgc tggccctgtg gctgcccaca gactcagcta ctgttctgca gaagatgaat
2881 gagatccagg ccattgcagc caggctcccc aacgtggact tggtgctgtc ccagaccaag
2941 caggacattg cgcgtgcccg ccggttgcag gctgaggctg aggaagccag gagccgagcc
3001 catgcagtgg agggccaggt ggaagatgtg gttgggaacc tgcggcaggg gacagtggca
3061 ctgcaggaag ctcaggacac catgcaaggc accagccgct cccttcggct tatccaggac
3121 agggttgctg aggttcagca ggtactgcgg ccagcagaaa agctggtgac aagcatgacc
3181 aagcagctgg gtgacttctg gacacggatg gaggagctcc gccaccaagc ccggcagcag
3241 ggggcagagg cagtccaggc ccagcagctt gcggaaggtg ccagcgagca ggcattgagt
3301 gcccaagagg gatttgagag aataaaacaa aagtatgctg agttgaagga ccggttgggt
3361 cagagttcca tgctgggtga gcagggtgcc cggatccaga gtgtgaagac agaggcagag
3421 gagctgtttg gggagaccat ggagatgatg gacaggatga agacatgga gttggagctg
3481 ctgcggggca gccaggccat catgctgcgc tcggcggacc tgacaggact ggagaagcgt
3541 gtggagcaga tccgtgacca catcaatggg cgcgtgctct actatgccac ctgcaagtga
3601 tgctacagct tccagcccgt tgccccactc atctgccgcc tttgcttttg gttgggggca
3661 gattgggttg gaatgctttc catctccagg agactttcat gcagcctaaa gtacagcctg
3721 gaccacccct ggtgtgtagc tagtaagatt accctgagct gcagctgagc ctgagccaat
3781 gggacagtta cacttgacag acaaagatgg tggagattgg catgccattg aaactaagag
3841 ctctcaagtc aaggaagctg ggctgggcag tatccccgc ctttagttct ccactgggga
3901 ggaatcctgg accaagcaca aaaacttaac aaaagtgatg taaaaatgaa aagccaaata
3961 aaaatctttg g
```

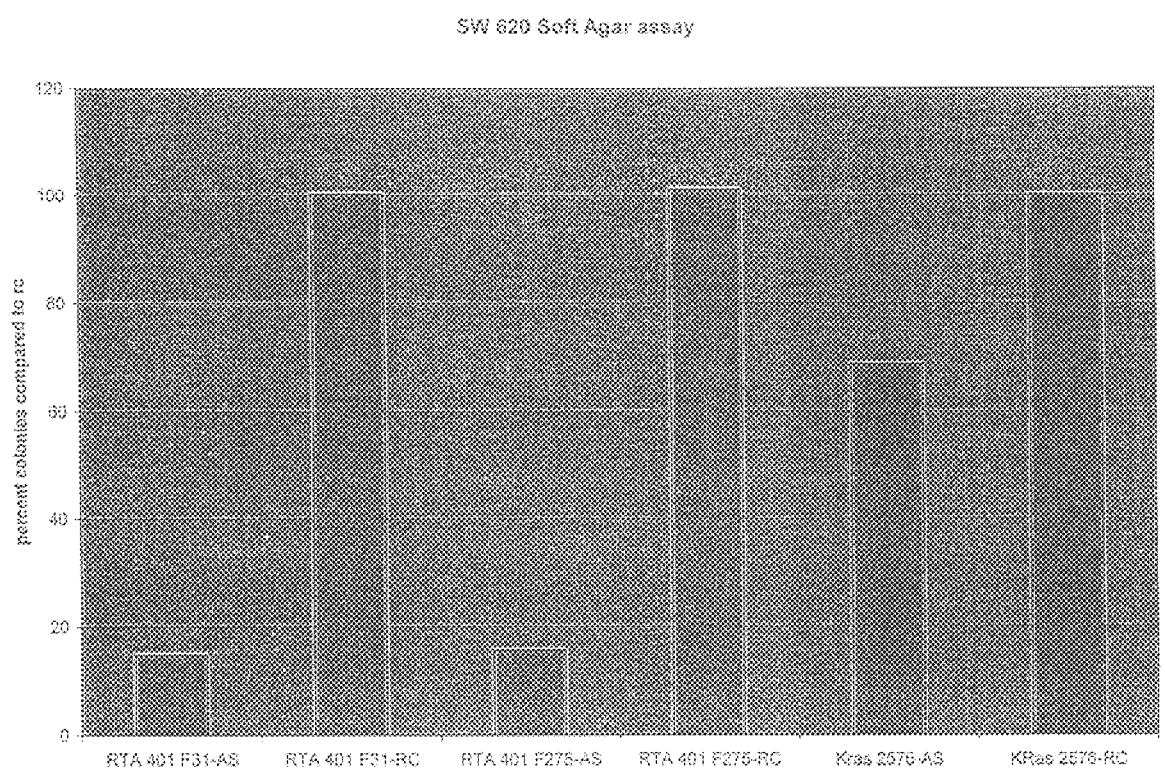

COMPOSITIONS AND METHODS FOR TREATING NEOPLASTIC DISEASE USING INHIBITORS OF LAMININ5BETA3

CROSS-REFERENCE TO RELATED APPLICATIONS

This application claims priority from U.S. Provisional Patent Application No. 60/210,409 filed Jun. 8, 2000, which is incorporated by reference herein in its entirety.

TECHNICAL FIELD

The invention provides compositions and methods for inhibiting laminin5beta3 gene expression and/or biological activity. Such compositions and methods find utility in the treatment of cancers, particularly of epithelial origin.

BACKGROUND OF THE INVENTION

A number of cancers derive from epithelial cells, including some colon cancers and breast cancers. Laminin is a secreted protein that plays a role in normal cell function by interacting with its integrin receptors. Laminins are heterotrimeric basement membrane molecules that mediate important cell functions including adhesion, migration and differentiation. Laminin5gamma2 has been found to play a role in cell adhesion of human keratinocytes and mouse squamous carcinoma cells. (Salo, S. et al., *Matrix Biol.* 18:197–210, 1999.) Alteration of laminin-5 expression was reported in development of squamous cell carcinomas. (Thorup, A. K. et al., *A.P.M.I.S.* 106:1170–1180, 1998.) Because of the role played by proteins of the laminin family in cancer cell development, there is a need in the art for materials and methods for regulating laminin expression and function, thereby providing new methods for cancer treatment and prevention.

SUMMARY OF THE INVENTION

The present invention provides, in one embodiment, inhibitors of laminin5beta3. Inventive inhibitors include, but are not limited to, antisense molecules, ribozymes, antibodies or antibody fragments, human monoclonal antibodies, proteins or polypeptides as well as small molecules. Exemplary antisense molecules comprise at least 10, 15 or 20 consecutive nucleotides of or hybridize under stringent conditions to the nucleic acid of SEQ ID NO: 1. More preferred are antisense molecules that comprise at least 25 consecutive nucleotides of or hybridize under stringent conditions to the sequence of SEQ ID NO:1. Representative antisense molecules are provided herein as SEQ ID NO:2 and 3.

In further embodiments, compositions are provided that comprise one or more laminin5beta3 inhibitor in a pharmaceutically acceptable carrier.

Additional embodiments provide methods of decreasing laminin5beta3 gene expression or biological activity.

Each of the methods of the present invention have in common the administration of one or more inventive laminin5beta3 inhibitor to a mammalian cell.

BRIEF DESCRIPTION OF THE FIGURES

FIG. 1 shows the polynucleotide sequence (SEQ ID NO:1) of laminin5beta3 cDNA.

FIG. 2A, 50 nM antisense oligonucleotide; FIG. 2B, 100 nM antisense oligonucleotide; FIG. 2C, 200 nM antisense oligonucleotide; FIG. 2D, 300 nM antisense oligonucleotide.

FIG. 5 is a bar graph illustrating that SW620 colon cancer cells transfected with antisense oligonucleotides SEQ ID NO:2 and 3 (F31-AS and F275-AS) showed inhibition of anchorage-independent growth. Control-transfected cells exhibited normal growth characteristics.

DETAILED DESCRIPTION OF THE INVENTION

Figure 2:
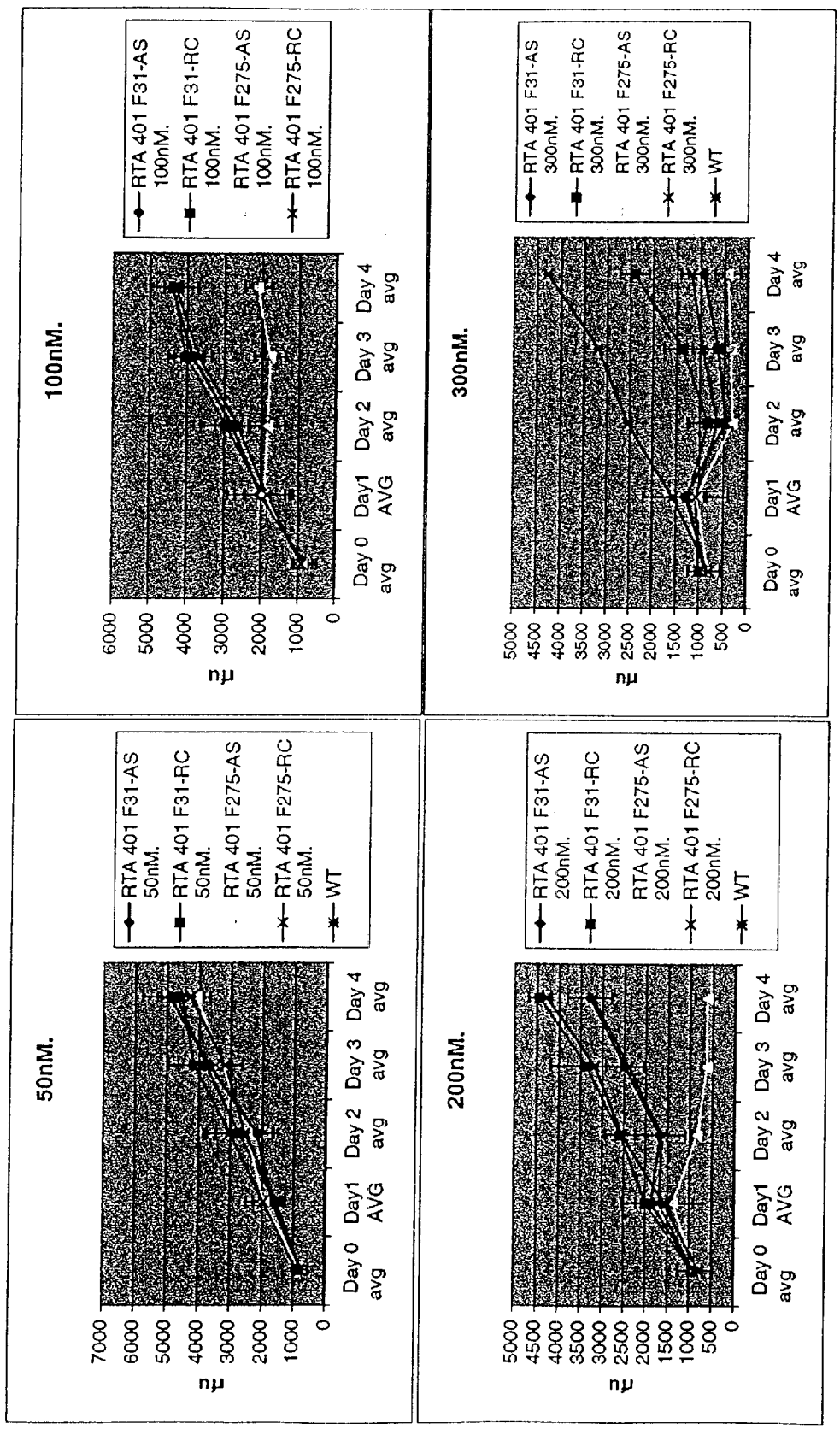
FIG. 2 illustrates that increasing levels of antisense oligonucleotides SEQ ID NO:2 and 3 correlated with decreased proliferation of SW620 colon carcinoma cells.

Laminin5beta3 is a member of the family of heterotrimeric basement membrane molecules that are involved in important cell functions such as adhesion, proliferation, migration, and differentiation. To date, five α, three β and two γ chain isoforms of laminin have been identified and these form at least 11 separate trimers. Lohi et al. *APMIS* 108:161–172, 2000, disclosed that carcinoma cells produce laminin-5, which is involved in cell adhesion to its integrin receptors. Three distinct laminins have been identified in the normal human small intestinal epithelium. Laminin-1 (alpha1beta1gamma1) and laminin-5 (alpha3beta3gamma2) are mainly expressed at the base of villus cells, whereas laminin-2 (alpha2beta1gamma1) is restricted to the bottom of the crypts. (Bovatrouss, Y. et al, *Am. J. Pathol* 156:45–50, 2000.)

The distribution of the laminin gamma2 chain was investigated in 48 different human gastric adenocarcinomas. The immunohistochemical analysis showed two patterns of laminin gamma2 chain expression: extracellular deposition and cytoplasmic accumulation. The extracellular deposition of the laminin gamma2 chain was observed at neoplastic basement membranes of well-differentiated adenocarcinomas. The immunoreactivity was continuous along tumor basement membranes in these tumors but was irregular and diffuse in poorly differentiated carcinomas. These tumor cells coexpressed the laminin alpha3 and beta3 chains, suggesting that the laminin gamma2 chain was deposited as the laminin-5 complex. In contrast, tumor cells at the invading fronts showed strong cytoplasmic staining for the laminin gamma2 chain without any detectable signal for the laminin alpha3 or beta3 chain in both well- and poorly differentiated carcinomas. In vitro analysis by two-dimensional SDS-PAGE demonstrated that human gastric carcinoma cells secrete a high level of laminin gamma2 chain monomer in addition to the laminin-5 complex into culture medium. (Koshikawa, N. et al., *Cancer Res.* 59:5596–5601, 1999.)

Skyldberg, B. et al. (*J. Natl. Cancer Inst.* 91:1882–1887, 1999) recently reported that invasiveness of cervical lesions was positively associated with immunohistochemical staining of the gamma2 chain of laminin-5. Lesions characterized as mild or moderate dysplasia (except one moderate lesion later shown to be invasive cancer) and 21 severe dysplasia lesions and all invasive cancers tested positive for this protein. One lymph node metastasis and a pleural metastasis from one of the patients with invasive cancer showed strong immunohistochemical positivity. Proliferative activity increased with advancement of the lesion but was not confined to cells positive for the gamma2 chain of laminin-5.

Lohi, J. et al., *APMIS* 108:161–172, 2000, reported that basement membrane laminin-5 is deposited in colorectal adenomas and carcinomas, and that it serves as a ligand for alpha3beta1 integrin.

The present invention substantially adds to the information about the role of laminin proteins in cancer and also provides methods and compositions for modulating cancer cell growth by inhibiting laminin5beta3 expression. Laminin5beta3 is expressed at a higher level in highly metastatic breast cancer cells than in breast cancer cells with low metastatic potential. To further investigate the role of laminin5beta3 expression in tumor cell growth, cells of colon cancer cell line SW620 were exposed to antisense molecules based on the sequence of laminin5beta3. As shown in FIG. 5, transfection of SW620 cells with antisense molecules 3-3 and 3-4 (SEQ ID NO:2 and 3) showed inhibition of anchorage-independent growth.

Antisense molecules 3-3 and 3-4 reduced laminin5beta3 mRNA levels in MDA231 cells, and reduced proliferation of MDA231 cells and SW620 cells. However, there was no effect on the proliferation of human fibrosarcoma cells. The results with cell lines correlate with expression of laminin5beta3 in human cancer tissue samples. Oligonucleotide probes specific for laminin5beta3 polynucleotides showed greater levels of in situ hybridization in breast, colon, and prostrate cancer samples. Further in situ analysis suggested that laminin5beta3 expression is up-regulated in cancerous lesions that originate in epithelial layers.

Antisense oligonucleotides based on the polynucleotide sequence of laminin5beta3 therefore are specific inhibitors of laminin5beta3 expression, and this correlates with decreased proliferation of colon cancer and breast cancer cells. Antisense oligonucleotides are suitable for in vivo treatment of colon cancer and other cancers, particularly those of epithelial origin, in which increased laminin5beta3 expression plays a role in cell growth, migration, metastasis, and survival. However, the invention is not limited to use of antisense inhibitors. Based on the results herein, other compositions and methods for inhibiting laminin5beta3 expression or for modulating or inhibiting laminin5beta3 function are also suitable for regulating cell proliferation. In particular, monoclonal antibodies, specifically humanized antibodies as disclosed herein, are useful, as laminin functions extracellularly in cell adhesion through interaction with its receptor integrin.

The present invention is directed generally to modulating laminin5beta3 expression and function, particularly in cancer cells, more particularly in breast, colon and prostate cancer cells. More specifically, the invention provides inhibitors of laminin5beta3, including antisense polynucleotides and ribozymes, proteins or polypeptides, antibodies or fragments thereof and small molecules; compositions comprising laminin5beta3 inhibitors; methods of supplementing chemotherapeutic and/or radiation treatment of a mammalian cell, as well as methods of treating neoplastic disease. Each of these methods have in common the administration to a mammalian cell of one or more laminin5beta3 inhibitor.

The polynucleotides of the invention can also be formulated as a diagnostic kit for detecting, for example, the expression of laminin5beta3 messenger RNA in a tumor cell. A diagnostic kit may contain at least one oligonucleotide capable of hybridizing to SEQ ID NO: 1 under stringent conditions. Preferably the polynucleotide will be at least 15 base pairs in length.

In a preferred embodiment, the kit will comprise at least one oligonucleotide selected from the group consisting of SEQ ID NOs:2 and 3, and at least one control oligonucleotide that does not hybridize with a polynucleotide of SEQ ID NO: 1 under stringent conditions.

Inhibitors of Laminin5beta3 are Effective in Reducing Laminin5beta3 Gene Expression Inventive laminin5beta3 inhibitors include antisense molecules and ribozymes, proteins or polypeptides, antibodies or fragments thereof as well as small molecules. Each of these laminin5beta3 inhibitors share the common feature that they reduce the expression and/or biological activity of laminin5beta3 and/or laminin-integrin binding and, as a consequence, modulate, inhibit, or prevent the growth of cancer cells. In addition to the exemplary laminin5beta3 inhibitors disclosed herein, alternative inhibitors may be obtained through routine experimentation utilizing methodology either specifically disclosed herein or as otherwise readily available to and within the expertise of the skilled artisan.

Antisense Molecules and Ribozymes

Laminin5beta3 inhibitors of the present invention include antisense molecules that, when administered to mammalian cells, are effective in reducing, for example, intracellular levels of laminin5beta3 mRNA. Antisense molecules bind in a sequence-specific manner to nucleic acids, such as mRNA or DNA. When bound to mRNA that has complementary sequences, antisense molecules prevent translation of the mRNA (see, e.g., U.S. Pat. No. 5,168,053 to Altman et al.; U.S. Pat. No. 5,190,931 to Inouye, U.S. Pat. No. 5,135,917 to Burch; U.S. Pat. No. 5,087,617 to Smith and Clusel et al. *Nucl. Acids Res.* 21:3405–3411 (1993), which describes dumbbell antisense oligonucleotides).

Antisense technology can be used to control gene expression through triple-helix formation, which promotes the ability of the double helix to open sufficiently for the binding of polymerases, transcription factors or regulatory molecules. See Gee et al., In Huber and Carr, "Molecular and Immunologic Approaches," Futura Publishing Co. (Mt. Kisco, N.Y.; 1994). Alternatively, an antisense molecule may be designed to hybridize with a control region of the laminin5beta3 gene, e.g., promoter, enhancer or transcription initiation site, and block transcription of the gene; or block translation by inhibiting binding of a transcript to ribosomes. See generally, Hirashima et al. in *Molecular Biology of RNA: New Perspectives* (M. Inouye and B. S. Dudock, eds., 1987 Academic Press, San Diego, p. 401); *Oligonucleotides: Antisense Inhibitors of Gene Expression* (J. S. Cohen, ed., 1989 MacMillan Press, London); Stein and Cheng, *Science* 261:1004–1012 (1993); WO 95/10607; U.S. Pat. No. 5,359,051; WO 92/06693; and EP-A2 and 312844, each of which is incorporated herein by reference.

Briefly, such molecules are constructed such that they are complementary to, and able to form Watson-Crick base pairs with, a region of transcribed laminin5beta3 mRNA sequence. The resultant double-stranded nucleic acid interferes with subsequent processing of the mRNA, thereby preventing protein synthesis.

In general, a portion of a sequence complementary to the laminin5beta3 coding region may be used to modulate gene expression. The sequence of laminin5beta3 cDNA is shown in SEQ ID NO: 1. Alternatively, cDNA constructs that can be transcribed into antisense RNA may be introduced into cells or tissues to facilitate the production of antisense RNA. Thus, as used herein, the phrase "antisense molecules" broadly encompasses antisense oligonucleotides whether synthesized as DNA or RNA molecules as well as all plasmid constructs that, when introduced into a mammalian cell, promote the production of antisense RNA molecules. An antisense molecule may be used, as described herein, to inhibit expression of mRNA or protein, as well as any other gene that requires laminin5beta3 for its expression.

The present invention relates to antisense oligonucleotides designed to interfere with the normal function of laminin5beta3 polynucleotides. Examples of preferred oligonucleotides are SEQ ID NO:2 and 3. Any modifications or variations of the antisense molecule which are known in the art to be broadly applicable to antisense technology are included within the scope of the invention. Such modifications include preparation of phosphorus-containing linkages as disclosed in U.S. Pat. Nos. 5,536,821; 5,541,306; 5,550,111; 5,563,253; 5,571,799; 5,587,361, 5,625,050 and 5,958,773.

The antisense compounds of the invention can include modified bases as disclosed in U.S. Pat. No. 5,958,773 and patents disclosed therein. The antisense oligonucleotides of the invention can also be modified by chemically linking the oligonucleotide to one or more moieties or conjugates to enhance the activity, cellular distribution, or cellular uptake of the antisense oligonucleotide. Such moieties or conjugates include lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585,481, 5,587,371, 5,597,696 and 5,958,773.

Chimeric antisense oligonucleotides are also within the scope of the invention, and can be prepared from the present inventive oligonucleotides using the methods described in, for example, U.S. Pat. Nos. 5,013,830, 5,149,797, 5,403,711, 5,491,133, 5,565,350, 5,652,355, 5,700,922 and 5,958,773.

In the antisense art a certain degree of routine experimentation is required to select optimal antisense molecules for particular targets. To be effective, the antisense molecule preferably is targeted to an accessible, or exposed, portion of the target RNA molecule. Although in some cases information is available about the structure of target mRNA molecules, the current approach to inhibition using antisense is via experimentation. According to the invention, this experimentation can be performed routinely by transfecting cells with an antisense oligonucleotide using methods described in Example 1. mRNA levels in the cell can be measured routinely in treated and control cells by reverse transcription of the mRNA and assaying the cDNA levels. The biological effect can be determined routinely by measuring cell growth or viability as is known in the art.

Measuring the specificity of antisense activity by assaying and analyzing cDNA levels is an art-recognized method of validating antisense results. It has been suggested that RNA from treated and control cells should be reverse-transcribed and the resulting cDNA populations analyzed. (Branch, A. D., T.I.B.S. 23:45–50, 1998.) According to the present invention, cultures of MDA231 cells were transfected with antisense oligonucleotides designed to target laminin5beta3. These oligonucleotides are shown in SEQ ID NO:2 and 3. The levels of mRNA corresponding to laminin5beta3 were measured in treated and control cells. SEQ ID NO:2 and 3 caused dramatic decreases in laminin5beta3 mRNA when normalized to actin mRNA levels.

Antisense molecules for use as described herein can be synthesized by any method known to those of skill in this art including chemical synthesis by, for example, solid phase phosphoramidite chemical synthesis. See, e.g., WO 93/01286; U.S. Pat. Nos. 6,043.090; 5,218,088; 5,175,269; and 5,109,124, each of which is incorporated herein by reference. Alternatively, RNA molecules may be generated by in vitro or in vivo transcription of DNA sequences encoding the laminin5beta3 cDNA, or a portion thereof, provided that the DNA is incorporated into a vector downstream of a suitable RNA polymerase promoter (such as, e.g., T3, T7 or SP6). Large amounts of antisense RNA may be produced by incubating labeled nucleotides with a linearized laminin5beta3 cDNA fragment downstream of such a promoter in the presence of the appropriate RNA polymerase. Such antisense molecules are preferably at least 10, 15 or 20 nucleotides in length. More preferably, antisense molecules are at least 25 nucleotides in length. Within certain embodiments, an antisense molecule of the present invention will comprise a sequence that is unique to the laminin5beta3 cDNA sequence of SEQ ID NO:1 or that can hybridize to the cDNA of SEQ ID NO:1 under conditions of high stringency. Within the context of the present invention, high stringency means standard hybridization conditions such as, e.g., 5×SSPE, 0.5% SDS at 65° C. or the equivalent thereof. See Sambrook et al., supra and *Molecular Biotechnology: Principles and Applications of Recombinant DNA*, supra incorporated herein by reference.

Antisense oligonucleotides are typically designed to resist degradation by endogenous nucleolytic enzymes by using such linkages as: phosphorothioate, methylphosphonate, sulfone, sulfate, ketyl, phosphorodithioate, phosphoramidate, phosphate esters, and other such linkages (see, e.g., Agrwal et al., *Tetrehedron Lett.* 28:3539–3542 (1987); Miller et al., *J. Am. Chem. Soc.* 93:6657–6665 (1971); Stec et al., *Tetrehedron Lett.* 26:2191–2194 (1985); Moody et al., *Nucl. Acids Res.* 12:4769–4782 (1989); Uznanski et al., *Nucl. Acids Res.* 17(12):4863–4871 (1989); Letsinger et al., *Tetrahedron* 40:137–143 (1984); Eckstein, *Annu. Rev. Biochem.* 54:367–402 (1985); Eckstein, *Trends Biol. Sci.* 14:97–100 (1989); Stein, in: *Oligodeoxynucleotides. Antisense Inhibitors of Gene Expression*, Cohen, Ed, Macmillan Press, London, pp. 97–117 (1989); Jager et al., *Biochemistry* 27:7237–7246 (1988)). Possible additional or alternative modifications include, but are not limited to, the addition of flanking sequences at the 5' and/or 3' ends and/or the inclusion of nontraditional bases such as inosine, queosine and wybutosine, as well as acetyl- methyl-, thio- and other modified forms of adenine, cytidine, guanine, thymine and uridine.

Within alternate embodiments of the present invention, laminin5beta3 inhibitors may be ribozymes. A ribozyme is an RNA molecule that specifically cleaves RNA substrates, such as mRNA, resulting in specific inhibition or interference with cellular gene expression. As used herein, the term "ribozymes" includes RNA molecules that contain antisense sequences for specific recognition, and an RNA-cleaving enzymatic activity. The catalytic strand cleaves a specific site in a target RNA at greater than stoichiometric concentration.

A wide variety of ribozymes may be utilized within the context of the present invention, including for example, the hammerhead ribozyme (for example, as described by Forster and Symons, *Cell* 48:211–220 (1987); Haseloff and Gerlach, *Nature* 328:596–600 (1988); Walbot and Bruening, *Nature* 334:196 (1988); Haseloff and Gerlach, *Nature* 334:585 (1988)); the hairpin ribozyme (for example, as described by Haseloff et al., U.S. Pat. No. 5,254,678, issued Oct. 19, 1993 and Hempel et al., European Patent Publication No. 0 360 257, published Mar. 26, 1990); and *Tetrahymena* ribosomal RNA-based ribozymes (see Cech et al., U.S. Pat. No. 4,987,071). Ribozymes of the present invention typically consist of RNA, but may also be composed of DNA, nucleic acid analogs (e.g., phosphorothioates), or chimerics thereof (e.g., DNA/RNA/RNA).

Ribozymes can be targeted to any RNA transcript and can catalytically cleave such transcripts (see, e.g., U.S. Pat. Nos. 5,272,262; 5,144,019; and 5,168,053, 5,180,818, 5,116,742 and 5,093,246 to Cech et al.). According to certain embodiments of the invention, any such laminin5beta3 mRNA-specific ribozyme, or a nucleic acid encoding such a ribozyme, may be delivered to a host cell to effect inhibition of laminin5beta3 gene expression. Ribozymes and the like may therefore be delivered to the host cells by DNA encoding the ribozyme linked to a eukaryotic promoter, such as a eukaryotic viral promoter, such that upon introduction into the nucleus, the ribozyme will be directly transcribed.

Proteins and Polypeptides

In addition to the antisense molecules and ribozymes disclosed herein, laminin5beta3 inhibitors of the present invention also include proteins or polypeptides that are effective in either reducing laminin5beta3 gene expression or in decreasing one or more of laminin5beta3's biological activities. A variety of methods are readily available in the art by which the skilled artisan may, through routine experimentation, rapidly identify such laminin5beta3 inhibitors. The present invention is not limited by the following exemplary methodologies.

Inhibitors of laminin5beta3's biological activities encompass those proteins and/or polypeptides that interfere with cell proliferation, particularly tumor cell proliferation, especially colon cell proliferation. Such interference may occur indirectly through non- or un-competitive inhibition such as via binding to an allosteric site, or by binding to a region that normally binds to another protein. Accordingly, available methods for identifying proteins and/or polypeptides that bind to laminin5beta3 may be employed to identify lead compounds that may, through the methodology disclosed herein, be characterized for their laminin5beta3 inhibitory activity.

A vast body of literature is available to the skilled artisan that describes methods for detecting and analyzing protein-protein interactions. Reviewed in Phizicky, E. M. et al., *Microbiological Reviews* 59:94–123 (1995) incorporated herein by reference. Such methods include, but are not limited to physical methods such as, e.g., protein affinity chromatography, affinity blotting, immunoprecipitation and cross-linking as well as library-based methods such as, e.g., protein probing, phage display and two-hybrid screening. Other methods that may be employed to identify protein-protein interactions include genetic methods such as use of extragenic suppressors, synthetic lethal effects and unlinked noncomplementation. Exemplary methods are described in further detail below.

Inventive laminin5beta3 inhibitors may be identified through biological screening assays that rely on the direct interaction between the laminin5beta3 protein and a panel or library of potential inhibitor proteins. Biological screening methodologies, including the various "n-hybrid technologies," are described in, for example, Vidal, M. et al., *Nucl. Acids Res.* 27(4):919–929 (1999); Frederickson, R. M., *Curr. Opin. Biotechnol.* 9(1):90–6 (1998); Brachmann, R. K. et al., *Curr. Opin. Biotechnol* 8(5):561–568 (1997); and White, M. A., *Proc. Natl Acad. Sci. U.S.A.* 93:10001–10003 (1996) each of which is incorporated herein by reference.

The two-hybrid screening methodology may be employed to search new or existing target cDNA libraries for laminin5beta3 binding proteins that have inhibitory properties. The two-hybrid system is a genetic method that detects protein-protein interactions by virtue of increases in transcription of reporter genes. The system relies on the fact that site-specific transcriptional activators have a DNA-binding domain and a transcriptional activation domain. The DNA-binding domain targets the activation domain to the specific genes to be expressed. Because of the modular nature of transcriptional activators, the DNA-binding domain may be severed covalently from the transcriptional activation domain without loss of activity of either domain. Furthermore, these two domains may be brought into juxtaposition by protein-protein contacts between two proteins unrelated to the transcriptional machinery. Thus, two hybrids are constructed to create a functional system. The first hybrid, i.e., the bait, consists of a transcriptional activator DNA-binding domain fused to a protein of interest. The second hybrid, the target, is created by the fusion of a transcriptional activation domain with a library of proteins or polypeptides. Interaction between the bait protein and a member of the target library results in the juxtaposition of the DNA-binding domain and the transcriptional activation domain and the consequent up-regulation of reporter gene expression.

A variety of two-hybrid based systems are available to the skilled artisan that most commonly employ either the yeast Gal4 or *E. coli* LexA DNA-binding domain (BD) and the yeast Gal4 or herpes simplex virus VP16 transcriptional activation domain. Chien, C.-T. et al., *Proc. Natl. Acad. Sci. U.S.A.* 88:9578–9582 (1991); Dalton, S. et al., *Cell* 68:597–612 (1992); Durfee, T. K. et al., *Genes Dev.* 7:555–569 (1993); Vojtek, A. B. et al., *Cell* 74:205–214 (1993); and Zervos, A. S. et al., *Cell* 72:223–232 (1993). Commonly used reporter genes include the *E. coli* lacZ gene as well as selectable yeast genes such as HIS3 and LEU2. Fields, S. et al., *Nature* (London) 340:245–246 (1989); Durfee, T.K., supra; and Zervos, A.S., supra. A wide variety of activation domain libraries are readily available in the art such that the screening for interacting proteins may be performed through routine experimentation.

Suitable bait proteins for the identification of laminin5beta3 interacting proteins may be designed based on the laminin5beta3 cDNA sequence presented herein as SEQ ID NO: 1. Such bait proteins include either the full-length laminin5beta3 protein or fragments thereof.

Plasmid vectors, such as, e.g., pBTM116 and pAS2–1, for preparing laminin5beta3 bait constructs and target libraries are readily available to the artisan and may be obtained from such commercial sources as, e.g., Clontech (Palo Alto, Calif.), Invitrogen (Carlsbad, Calif.) and Stratagene (La Jolla, Calif.). These plasmid vectors permit the in-frame fusion of cDNAs with the DNA-binding domains as LexA or Gal4BD, respectively.

Laminin5beta3 inhibitors of the present invention may alternatively be identified through one of the physical or biochemical methods available in the art for detecting protein-protein interactions.

Laminin5beta3 is believed to interact with the other cell surface proteins. Through the protein affinity chromatography methodology, lead compounds to be tested as potential laminin5beta3 inhibitors may be identified by virtue of their specific retention to laminin5beta3 when either covalently or non-covalently coupled to a solid matrix such as, e.g., Sepharose beads. The preparation of protein affinity columns is described in, for example, Beeckmans, S. et al., *Eur. J. Biochem.* 117:527–535 (1981) and Formosa, T. et al., *Methods Enzymol.* 208:24–45 (1991). Cell lysates containing the full complement of cellular proteins may be passed through the laminin5beta3 affinity column. Proteins having a high affinity for laminin5beta3 will be specifically retained under low-salt conditions while the majority of cellular proteins will pass through the column. Such high affinity proteins may be eluted from the immobilized laminin5beta3 under conditions of high-salt, with chaotropic solvents or with sodium dodecyl sulfate (SDS). In some embodiments, it may be preferred to radiolabel the cells prior to preparing the lysate as an aid in identifying the laminin5beta3 specific binding proteins. Methods for radiolabeling mammalian cells are well known in the art and are provided, e.g., in Sopta, M. et al., *J. Biol. Chem.* 260:10353–10360 (1985).

Suitable laminin5beta3 proteins for affinity chromatography may be fused to a protein or polypeptide to permit rapid purification on an appropriate affinity resin. For example, the laminin5beta3 cDNA may be fused to the coding region for glutathione S-transferase (GST) which facilitates the adsorption of fusion proteins to glutathione-agarose columns. Smith et al., Gene 67:31–40 (1988). Alternatively, fusion proteins may include protein A, which can be purified on columns bearing immunoglobulin G; oligohistidine-containing peptides, which can be purified on columns bearing $Ni^{2+}$; the maltose-binding protein, which can be purified on resins containing amylose; and dihydrofolate reductase, which can be purified on methotrexate columns. One exemplary tag suitable for the preparation of laminin5beta3 fusion proteins that is presented herein is the epitope for the influenza virus hemaglutinin (HA) against which monoclonal antibodies are readily available and from which antibodies an affinity column may be prepared.

Proteins that are specifically retained on a laminin5beta3 affinity column may be identified after subjecting to SDS polyacrylamide gel electrophoresis (SDS-PAGE). Thus, where cells are radiolabeled prior to the preparation of cell lysates and passage through the laminin5beta3 affinity column, proteins having high affinity for laminin5beta3 may be detected by autoradiography. The identity of laminin5beta3 specific binding proteins may be determined by protein sequencing techniques that are readily available to the skilled artisan, such as Mathews, C. K. et al., *Biochemistry*, The Benjamin/Cummings Publishing Company, Inc. pp.166–170 (1990).

Antibodies or Antibody Fragments

Laminin5beta3 inhibitors of the present invention include antibodies and/or antibody fragments that are effective in reducing laminin5beta3 gene expression and/or biological activity. Suitable antibodies may be monoclonal, polyclonal or humanized monoclonal antibodies. Antibodies may be derived by conventional hybridoma based methodology, from antisera isolated from laminin5beta3 inoculated animals or through recombinant DNA technology. Alternatively, inventive antibodies or antibody fragments may be identified in vitro by use of one or more of the readily available phage display libraries. Exemplary methods are disclosed herein.

In one embodiment of the present invention, laminin5beta3 inhibitors are monoclonal antibodies that may be produced as follows. Laminin5beta3 protein may be produced, for example, by expression of laminin5beta3 cDNA in a baculovirus based system. By this method, laminin5beta3 cDNA or a fragment thereof is ligated into a suitable plasmid vector that is subsequently used to transfect Sf9 cells to facilitate protein production. In addition, it may be advantageous to incorporate an epitope tag or other moiety to facilitate affinity purification of the laminin5beta3 protein. Clones of Sf9 cells expressing laminin5beta3 are identified, e.g., by enzyme linked immunosorbant assay (ELISA), lysates are prepared and the laminin5beta3 protein purified by affinity chromatography and the purified protein is injected, intraperitoneally, into BALB/c mice to induce antibody production. It may be advantageous to add an adjuvant, such as Freund's adjuvant, to increase the resulting immune response.

Serum is tested for the production of specific antibodies and spleen cells from animals having a positive specific antibody titer are used for cell fusions with myeloma cells to generate hybridoma clones. Supernatants derived from hybridoma clones are tested for the presence of monoclonal antibodies having specificity against laminin5beta3. For a general description of monoclonal antibody methodology, see, e.g., Harlow and Lane, *Antibodies: A Laboratory Manual*, Cold Spring Harbor Laboratory (1988).

In addition to the baculovirus expression system, other suitable bacterial or yeast expression systems may be employed for the expression of laminin5beta3 protein or polypeptides thereof. As with the baculovirus system, it may be advantageous to utilize one of the commercially available affinity tags to facilitate purification prior to inoculation of the animals. Thus, the laminin5beta3 cDNA or fragment thereof may be isolated by, e.g., agarose gel purification and ligated in frame with a suitable tag protein such as 6-His, glutathione-S-transferase (GST) or other such readily available affinity tag. See, e.g., *Molecular Biotechnology: Principles and Applications of Recombinant DNA*, ASM Press pp. 160–161 (ed. Glick, B. R. and Pasternak, J. J. 1998).

In other embodiments of the present invention, laminin5beta3 inhibitors are humanized anti-laminin5beta3 monoclonal antibodies. The phrase "humanized antibody" refers to an antibody derived from a non-human antibody—typically a mouse monoclonal antibody. Alternatively, a humanized antibody may be derived from a chimeric antibody that retains or substantially retains the antigen-binding properties of the parental, non-human, antibody but which exhibits diminished immunogenicity as compared to the parental antibody when administered to humans. The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

Because humanized antibodies are far less immunogenic in humans than the parental mouse monoclonal antibodies, they can be used for the treatment of humans with far less risk of anaphylaxis. Thus, these antibodies may be preferred in therapeutic applications that involve in vivo administration to a human such as, e.g., use as radiation sensitizers for the treatment of neoplastic disease or use in methods to reduce the side effects of, e.g., cancer therapy.

Humanized antibodies may be achieved by a variety of methods including, for example: (1) grafting the non-human complementarity determining regions (CDRs) onto a human framework and constant region (a process referred to in the art as "humanizing"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. These methods are disclosed in, e.g., Jones et al., *Nature* 321:522–525 (1986); Morrison et al., *Proc. Natl. Acad. Sci., U.S.A.*, 81:6851–6855 (1984); Morrison and Oi, *Adv. Immunol.*, 44:65–92 (1988); Verhoeyer et al., *Science* 239:1534–1536 (1988); Padlan, *Molec. Immun.* 28:489–498 (1991); Padlan,

*Molec. Immunol.* 31(3):169–217 (1994); and Kettleborough, C. A. et al., *Protein Eng.* 4(7):773–83 (1991) each of which is incorporated herein by reference.

The phrase "complementarity determining region" refers to amino acid sequences which together define the binding affinity and specificity of the natural Fv region of a native immunoglobulin binding site. See, e.g., Chothia et al., *J. Mol. Biol.* 196:901–917 (1987); Kabat et al., U.S. Dept. of Health and Human Services NIH Publication No. 91–3242 (1991). The phrase "constant region" refers to the portion of the antibody molecule that confers effector functions. In the present invention, mouse constant regions are substituted by human constant regions. The constant regions of the subject humanized antibodies are derived from human immunoglobulins. The heavy chain constant region can be selected from any of the five isotypes: alpha, delta, epsilon, gamma or mu.

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors. See, e.g., U.S. Pat. Nos. 5,530,101 and 5,585,089 which patents are incorporated herein by reference.

Humanized antibodies to laminin5beta3 can also be produced using transgenic animals that are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy claims, and express an exogenous immunoglobulin locus comprising one or more xenogeneic constant regions.

Using a transgenic animal described above, an immune response can be produced to a selected antigenic molecule, and antibody-producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL-6, IL-8, TNFα, human CD4, L-selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8-induced functions of neutrophils. Human monoclonal antibodies with specificity for the antigen used to immunize transgenic animals are also disclosed in WO 96/34096.

In the present invention, laminin5beta3 polypeptides of the invention and variants thereof are used to immunize a transgenic animal as described above. Monoclonal antibodies are made using methods known in the art, and the specificity of the antibodies is tested using isolated laminin5beta3 polypeptides. The suitability of the antibodies for clinical use is tested by, for example, exposing SW620 cells to the antibodies and measuring cell growth. According to the invention, inhibition of laminin5beta3 expression using antisense oligonucleotides specific for laminin5beta3 polynucleotides causes an inhibition of anchorage-independent growth of a colon cancer cell line, SW620. The antisense oligonucleotides also inhibited the proliferation of a breast cancer cell line, MDA231, and SW620 cells. Human monoclonal antibodies specific for laminin5beta3 or a variant or fragment thereof can be tested for their ability to inhibit proliferation, colony growth, or any other biological parameter indicative of control of tumor growth, migration, or metastasis, particularly tumor cells of epithelial origin. Such antibodies would be suitable for pre-clinical and clinical trials as pharmaceutical agents for preventing or controlling growth of cancer cells.

It will be appreciated that alternative laminin5beta3 inhibitor antibodies may be readily obtained by other methods commonly known in the art. One exemplary methodology for identifying antibodies having a high specificity for laminin5beta3 is the phage display technology.

Phage display libraries for the production of high-affinity antibodies are described in, for example, Hoogenboom, H. R et al., *Immunotechnology* 4(I):1–20 (1998); Hoogenboom, H. R., *Trends Biotechnol.* 15:62–70 (1997) and McGuinness, B. et al., *Nature Bio. Technol.* 14:1149–1154 (1996) each of which is incorporated herein by reference. Among the advantages of the phage display technology is the ability to isolate antibodies of human origin that cannot otherwise be easily isolated by conventional hybridoma technology. Furthermore, phage display antibodies may be isolated in vitro without relying on an animal's immune system.

Antibody phage display libraries may be accomplished, for example, by the method of McCafferty et al., *Nature* 348:552–554 (1990) which is incorporated herein by reference. In short, the coding sequence of the antibody variable region is fused to the amino terminus of a phage minor coat protein (pIII). Expression of the antibody variable regionpIII fusion construct results in the antibody's "display" on the phage surface with the corresponding genetic material encompassed within the phage particle.

Laminin5beta3 protein suitable for screening a phage library may be obtained by, for example, expression in baculovirus Sf9 cells as described, supra. Alternatively, the laminin5beta3 coding region may be PCR amplified using primers specific to the desired region of the laminin5beta3 protein. As discussed above, the laminin5beta3 protein may be expressed in *E. coli* or yeast as a fusion with one of the commercially available affinity tags.

The resulting fusion protein may then be adsorbed to a solid matrix, e.g., a tissue culture plate or bead. Phage expressing antibodies having the desired anti-laminin5beta3 binding properties may subsequently be isolated by successive panning, in the case of a solid matrix, or by affinity adsorption to a laminin5beta3 antigen column. Phage having the desired laminin5beta3 inhibitory activities may be reintroduced into bacteria by infection and propagated by standard methods known to those skilled in the art. See Hoogenboom, H. R., *Trends Biotechnol.*, supra for a review of methods for screening for positive antibody-pIII phage.

Small Molecules

The present invention also provides small molecule laminin5beta3 inhibitors that may be readily identified through routine application of high-throughput screening (HTS) methodologies. Reviewed by Persidis, A., *Nature Biotechnology* 16:488–489 (1998). HTS methods generally refer to those technologies that permit the rapid assaying of lead compounds, such as small molecules, for therapeutic potential. HTS methodology employs robotic handling of test materials, detection of positive signals and interpretation of data. Such methodologies include, e.g., robotic screening technology using soluble molecules as well as cell-based systems such as the two-hybrid system described in detail above.

A variety of cell line-based HTS methods are available that benefit from their ease of manipulation and clinical relevance of interactions that occur within a cellular context as opposed to in solution. Lead compounds may be identified via incorporation of radioactivity or through optical assays that rely on absorbance, fluorescence or luminescence as read-outs. See, e.g., Gonzalez, J. E. et al., *Curr. Opin. Biotechnol.* 9(6):624–631 (1998) incorporated herein by reference.

HTS methodology may be employed, e.g., to screen for lead compounds that block one of laminin5beta3's biological activities, particularly its ability to interact with other cell-surface proteins. By this method, laminin5beta3 protein may be immunoprecipitated from cells expressing the protein and applied to wells on an assay plate suitable for robotic screening. Individual test compounds may then be contacted with the immunoprecipitated protein and the effect of each test compound on laminin5beta3 activity, such as the ability to bind to integrin (receptor), assessed.

Methods for Assessing the Efficacy of Laminin5beta3 Inhibitors

Lead molecules or compounds, whether antisense molecules or ribozymes, proteins and/or peptides, antibodies and/or antibody fragments or small molecules, that are identified either by one of the methods described herein or via techniques that are otherwise available in the art, may be further characterized in a variety of in vitro, ex vivo and in vivo animal model assay systems for their ability to inhibit laminin5beta3 gene expression or biological activity. As discussed in further detail in the Examples, laminin5beta3 inhibitors of the present invention are effective in reducing laminin5beta3 expression levels and inhibiting cancer cell proliferation. Thus, the present invention further discloses methods that permit the skilled artisan to assess the effect of candidate inhibitors on each of these parameters.

As noted above and as presented in the Examples, candidate laminin5beta3 inhibitors may be tested by administration to cells that either express endogenous laminin5beta3 or that are made to express laminin5beta3 by transfection of a mammalian cell, such as MDA231 or SW620, with a recombinant laminin5beta3 plasmid construct.

Effective laminin5beta3 inhibitory molecules will reduce the levels of laminin5beta3 mRNA as determined, e.g., by Northern blot or RT-PCR analysis. See Example 1; for a general description of these procedures, see, e.g., Sambrook et al., *Molecular Cloning: A Laboratory Manual* Cold Spring Harbor Press (1989) and *Molecular Biotechnology: Principles and Applications of Recombinant DNA*, ASM Press (ed. Glick, B. R. and Pasternak, J. J. 1998) incorporated herein by reference, or may reduce the levels of laminin5beta3 protein in the cell. The effectiveness of a given candidate antisense molecule may be assessed by comparison with a control "antisense" molecule known to have no substantial effect on laminin5beta3 expression when administered to a mammalian cell. Exemplary control molecules include the RC oligonucleotides disclosed as SEQ ID NO:4 and 5.

Laminin5beta3 inhibitors effective in reducing laminin5beta3 gene expression and/or cell proliferation by one or more of the methods discussed herein may be further characterized in vivo for efficacy in one of the readily available animal model systems. The various animal model systems for study of cancer and genetic instability associated genes are discussed in, for example, Donehower, L. A. *Cancer Surveys* 29:329–352 (1997) incorporated herein by reference.

Administration of Laminin5beta3 Inhibitors and Compositions Thereof

The present invention provides laminin5beta3 inhibitors and compositions comprising one or more laminin5beta3 inhibitor as well as methods that employ these inventive inhibitors in in vivo, ex vivo, and in vitro applications where it is advantageous to reduce or eliminate the expression or activity of laminin5beta3 or a functionally downstream molecule. laminin5beta3 inhibitors may find use as drugs for supplementing cancer therapeutics and other agents. Laminin5beta3 inhibitors may also find use in other diseases of hyperproliferation, such as conditions of epithelial hyperplasia such as found in breast tissue.

Compositions may be administered parenterally, topically, orally or locally for therapeutic treatment. Preferably, the compositions are administered orally or parenterally, i.e., intravenously, intraperitoneally, intradermally or intramuscularly.

Inventive compositions will include one or more laminin5beta3 inhibitor and may further comprise a pharmaceutically acceptable carrier or excipient. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Laminin5beta3 inhibitors useful in the treatment of disease in mammals will often be prepared substantially free of other naturally occurring immunoglobulins or other biological molecules. Preferred laminin5beta3 inhibitors will also exhibit minimal toxicity when administered to a mammal.

The compositions of the invention may be sterilized by conventional, well known sterilization techniques. The resulting solutions may be packaged for use or filtered under aseptic conditions and lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride and stabilizers (e.g., 1–20% maltose, etc.).

The selection of the appropriate method for administering laminin5beta3 inhibitors of the present invention will depend on the nature of the application envisioned as well as the nature of the laminin5beta3 inhibitor. Thus, for example, the precise methodology for administering a laminin5beta3 inhibitor will depend upon whether it is an antisense molecule, a protein and/or peptide, an antibody or antibody fragment or a small molecule. Other considerations include, for example, whether the laminin5beta3 inhibitor will be used to inhibit tumor cell growth, invasion, or metastasis, or as an adjunct to other cancer therapeutics.

A variety of methods are available in the art for the administration of antisense molecules. Exemplary methods include gene delivery techniques, including both viral and non-viral based methods as well as liposome mediated delivery methods.

Gene delivery methodologies will be effective to, for example, reduce tumor cell proliferation, or supplement radiation and/or chemotherapeutic treatment of tumors. See, Wheldon, T. E. et al., *Radiother Oncol* 48(1):5–13 (1998) (gene delivery methodologies for enhancement of fractionated radiotherapy). By these methodologies, substantial therapeutic benefit may be achieved despite transfection efficiencies significantly less than 100%, transient retention of the transfected inhibitor and/or existence of a subpopulation of target cells refractory to therapy.

Alternatively, gene delivery methodology may be used to directly knock-out endogenous laminin5beta3 within tumor cells. For example, the laminin5beta3 gene may be targeted by transfection of a gene delivery vector carrying a laminin5beta3 inhibitor. Preferential transfection into or expression within tumor cells may be achieved through use of a tissue-specific or cell cycle-specific promoter, such as, e.g., promoters for prostate-specific antigen or for immunoglobulin genes (Vile, R. G. et al., *Cancer Res.* 53:962–967 (1993) and Vile, R. G., *Semin. Cancer Biol.* 5:437–443 (1994)) or through the use of trophic viruses that are confined to particular organs or structures, such as, e.g., a replication selective and neurotrophic virus that can only infect proliferating cells in the central nervous system.

Thus, to achieve therapeutic benefit, laminin5beta3 within the tumor cells should be preferentially inhibited. This can be accomplished by transfecting a gene expressing a laminin5beta3 inhibitor, a laminin5beta3 antisense molecule, a laminin5beta3 gene specific repressor, or an inhibitor of the protein product of the laminin5beta3 gene.

As used herein, the phrase "gene delivery vector" refers generally to a nucleic acid construct that carries and, within certain embodiments, is capable of directing the expression of an antisense molecule of interest, as described in, for example, *Molecular Biotechnology: Principles and Applications of Recombinant DNA*, Ch. 21, pp. 555–590 (ed. B. P. Glick and J. J. Pasternak, $2^{nd}$ ed. 1998); Jolly, *Cancer Gene Ther.* 1:51–64 (1994); Kimura, *Human Gene Ther.* 5:845–852 (1994); Connelly, *Human Gene Ther.* 6:185–193 (1995); and Kaplitt, *Nat. Gen.* 6:148–153 (1994).

A number of virus and non-virus based gene delivery vector systems have been described that are suitable for the administration of laminin5beta3 inhibitors. Virus based gene delivery systems include, but are not limited to retrovirus, such as Moloney murine leukemia virus, spumaviruses and lentiviruses; adenovirus; adeno-associated virus; and herpes-simplex virus vector systems. Viruses of each type are readily available from depositories or collections such as the American Type Culture Collection (ATCC; 10801 University Boulevard, Manassas, Va. 20110–2209) or may be isolated from known sources using commonly available materials and techniques.

The gene delivery vector systems of the present invention will find applications both in in vivo as well as ex vivo therapeutic regimens. Each of these applications is described in further detail below.

1. Retroviral Gene Delivery Vector Systems

Within one aspect of the present invention, retroviral gene delivery vectors are provided that are constructed to carry or express a laminin5beta3 inhibitory antisense molecule. As used herein, the term "laminin5beta3 inhibitory antisense molecule" refers generally to a nucleic acid sequence having laminin5beta3 inhibitory activity. More specifically, such antisense molecules will reduce laminin5beta3 gene expression. Retroviral gene delivery vectors of the present invention may be readily constructed from a wide variety of retroviruses, including for example, B, C, and D type retroviruses as well as spumaviruses and lentiviruses. See *RNA Tumor Viruses*, Cold Spring Harbor Laboratory ($2^{nd}$ ed.1985).

Any of the above retroviruses may be readily utilized in order to assemble or construct retroviral gene delivery vectors given the disclosure provided herein, and standard recombinant DNA techniques. See, e.g., Sambrook et al, *Molecular Cloning: A Laboratory Manual,* Cold Spring Harbor Laboratory Press (2d ed. 1989) and Kunkle, *Proc. Natl. Acad. Sci. U.S.A.* 82:488 (1985). In addition, within certain embodiments of the invention, portions of the retroviral gene delivery vectors may be derived from different retroviruses.

A retroviral vector, suitable for the expression of a laminin5beta3 inhibitory antisense molecule, must include at least one transcriptional promoter/enhancer or locus defining element(s), or other elements that control gene expression by other means such as alternate splicing, nuclear RNA export, post-translational modification of messenger, or post-transcriptional modification of protein. Such vector constructs must also include a packaging signal, long terminal repeats (LTRs) or portion thereof, and positive and negative strand primer binding sites appropriate to the retrovirus used (if these are not already present in the retroviral vector). Optionally, the retroviral vector may also include a signal that directs polyadenylation, selectable markers such as Neomycin resistance, TK, hygromycin resistance, phleomycin resistance histidinol resistance, or DHFR, as well as one or more restriction sites and a translation termination sequence. Within one aspect of the present invention, retroviral gene delivery vector constructs are provided comprising a 5' LTR, a tRNA binding site, a packaging signal, one or more heterologous sequences, an origin of second strand DNA synthesis and a 3' LTR, wherein the vector construct lacks gag/pol or env coding sequences.

Other retroviral gene delivery vectors may likewise be utilized within the context of the present invention, including, for example, those disclosed in the following each of which is incorporated herein by reference: EP 0,415,731; WO 90/07936; WO 94/03622; WO 93/25698; WO 93/25234; U.S. Pat. No. 5,219,740; WO 93/11230; WO 93/10218; Vile et al., *Cancer Res.* 53:3860–3864 (1993); Vile et al., *Cancer Res.* 53:962–967 (1993); Ram et al., *Cancer Res.* 53:83–88 (1993); Takamiya et al., *J. Neurosci. Res.* 33:493–503 (1992); Baba et al., *J. Neurosurg. Res.* 79:729–735 (1993); U.S. Pat. No. 4,777,127, GB 2,200,651, EP 0,345,242 and WO 91/02805.

Packaging cell lines suitable for use with the above described retroviral gene delivery vector constructs may be readily prepared. See, e.g., U.S. Pat. Nos. 5,716,832 and 5,591,624. These packaging cell lines may be utilized to create producer cell lines (also termed vector cell lines or "VCLs") for the production of recombinant vector particles.

It may be preferred to use packaging cell lines made from human (e.g., HT1080 cells) or mink parent cell lines, thereby allowing production of recombinant retroviruses that avoid inactivation in human serum.

2. Adeno-Associated Viral Gene Delivery Vector Systems

Adeno-associated viruses (AAV) possess a number of qualities that make them particularly suitable for the development of gene delivery vectors generally and for the delivery of polynucleotides encoding laminin5beta3 inhibitory antisense molecules in particular. For a general review of AAV expression systems, see Rabinowitz et al., *Current Opin. Biotech.* 9(5):470–475 (1998). AAV is a non-pathogenic, defective human parvovirus that is non-infective without an adeno or herpes helper virus. Thus, in the absence of a helper virus, AAV becomes integrated latently into the host genome. In addition, AAV has the advantage over the retroviruses, discussed above, in being able to transduce a wide range of both dividing and quiescent cell types.

A variety of AAV gene delivery vectors may be utilized to direct the expression of one or more laminin5beta3 inhibitor antisense molecule. Representative examples of such vectors include the AAV vectors disclosed by Srivastava in WO 93/09239; Samulski, et al. *J. Virol.* 63:3822–3828 (1989); Mendelson, et al. *Virol.* 166:154–165 (1988); and Flotte, et al. *Proc. Natl. Acad. Sci. U.S.A.* 90(22):10613–10617 (1993) incorporated herein by reference.

Briefly, an AAV gene delivery vector of the present invention may include, in order, a 5' adeno-associated virus inverted terminal repeat; a polynucleotide encoding the laminin5beta3 inhibitory antisense molecule; a sequence operably linked to the laminin5beta3 inhibitory antisense molecule that regulates its expression in a target tissue, organ or cell; and a 3' adeno-associated virus inverted terminal repeat. A suitable regulatory sequence for the expression of laminin5beta3 inhibitory antisense molecule is, e.g., the enhancer/promoter sequence of cytomegalovirus (CMV). In addition, the AAV vector may preferably have a polyadenylation sequence such as the bovine growth hormone (BGH) polyadenylation sequence.

Generally, AAV vectors should have one copy of the AAV ITR at each end of the laminin5beta3 inhibitory antisense molecule, to allow replication, packaging, efficient integration into the host cell genome and rescue from the chromosome. The 5' ITR sequence consists of nucleotides 1 to 145 at the 5' end of the AAV DNA genome, and the 3' ITR includes nucleotides 4681 to 4536 of the AAV genome. Preferably, the AAV vector may also include at least 10 nucleotides following the end of the ITR (i.e., a portion of the so-called "D region").

Optimal packaging of an adeno-associated virus gene delivery vector requires that the 5' and 3' ITRs be separated by approximately 2–5 kb. It will be apparent, however, that the ideal spacing between ITR sequences may vary depending on the particular packaging system utilized. This spacing may be achieved by incorporating a "stuffer" or "filler" polynucleotide fragment to bring the total size of the nucleic acid sequence between the two ITRs to between 2 and 5 kb. Thus, where the laminin5beta3 inhibitory antisense molecule is smaller than 2–5 kb, a non-coding stuffer polynucleotide may be incorporated, for example, 3' to the 5' ITR sequence and 5' of the laminin5beta3 inhibitory antisense molecule. The precise nucleotide sequence of the stuffer fragment is not an essential element of the final construct.

Depending upon the precise application contemplated, rather than incorporating a stuffer fragment, multiple copies of the laminin5beta3 inhibitory antisense molecule may be inserted, inter alia, to achieve the optimal ITR sequence spacing. It may be preferred to organize the polynucleotides as two or more separate transcription units each with its own promoter and polyadenylation signal.

Recombinant AAV vectors of the present invention may be generated from a variety of adeno-associated viruses, including for example, serotypes 1 through 6. For example, ITRs from any AAV serotype are expected to have similar structures and functions with regard to replication, integration, excision and transcriptional mechanisms.

Within certain embodiments of the invention, expression of the laminin5beta3 inhibitory antisense molecule may be accomplished by a separate promoter (e.g., a viral promoter). Representative examples of suitable promoters in this regard include a CMV promoter, an RSV promoter, an SV40 promoter, or a MoMLV promoter. Other promoters that may similarly be utilized within the context of the present invention include cell or tissue specific promoters or inducible promoters. Representative inducible promoters include tetracycline-response promoters (e.g., the "Tet" promoter) as described in Gossen et al., *Proc. Natl Acad. Sci. U.S.A.* 89:5547–5551 (1992); Gossen et al., *Science* 268:1766–1769 (1995); Baron et al., *Nucl. Acids Res.* 25:2723–2729 (1997); Blau et al., *Proc. Natl. Acad. Sci. U.S.A.* 96:797–799 (1999); Bohl et al., *Blood* 92:1512–1517 (1998); and Haberman et al., *Gene Therapy* 5:1604–1611 (1998); the ecdysone promoter system as described in No et al., *Proc. Natl. Acad. Sci. U.S.A.* 93:3346–3351 (1996); and other regulated promoters or promoter systems as described in Rivera et al., *Nat. Med.* 2:1028–1032 (1996).

The AAV gene delivery vector may also contain additional sequences, for example from an adenovirus, which assist in effecting a desired function for the vector. Such sequences include, for example, those which assist in packaging the AAV gene delivery vector in adenovirus particles.

Packaging cell lines suitable for producing adeno-associated viral vectors may be routinely prepared given readily available techniques. See, e.g., U.S. Pat. No. 5,872, 005, incorporated herein by reference. At a minimum, suitable packaging systems for AAV gene delivery systems of the present invention will include the AAV replication and capsid genes.

Preferred packaging cell lines may contain both an AAV helper virus as well as an AAV gene delivery vector containing the laminin5beta3 inhibitory antisense molecule. For detailed descriptions of representative packaging cell line systems, see, e.g. Holscher, C. et al., *J. Virol.* 68:7169–7177 (1994); Clark, K. R et al., *Hum. Gene Ther.* 6:1329–1341 (1995); and Tamayosa, K. et al., *Hum. Gen. Ther.* 7:507–513 (1996) which are incorporated herein by reference.

Alternatively, packaging of AAV may be achieved in vitro in a cell free system to obviate transfection protocols or packaging cell lines. Such in vitro systems incorporate an AAV gene delivery vector bearing the laminin5beta3 inhibitory antisense molecule and a source of Rep-protein, capsid-protein and Adenovirus proteins that supply helper-viral functions. The latter proteins are typically supplied in the form of a cell extract. Representative in vitro systems are further described in Ding, L. et al., *Gen. Ther.* 4:1167–1172 (1997) and Zhou, Z. et al., *J. Virol.* 72:3241–3247 (1998) which are incorporated herein by reference.

3. Other Viral Gene Delivery Vector Systems

In addition to retroviral vectors and adeno-associated virus-based vectors, numerous other viral gene delivery vector systems may also be utilized for the expression of laminin5beta3 inhibitory antisense molecules. For example, within one embodiment of the invention adenoviral vectors may be employed. Representative examples of such vectors include those described by, for example, Berkner, *Biotechniques* 6:616–627 (1988); Rosenfeld et al., *Science* 252:431–434 (1991); WO 93/9191; Kolls et al., *Proc. Natl. Acad. Sci. U.S.A.* 91(1):215–219 (1994); Kass-Eisler et al., *Proc. Natl. Acad. Sci. U.S.A.* 90(24):11498–502 (1993); Guzman et al., *Circulation* 88(6):2838–48 (1993); Guzman et al., *Cir. Res.* 73(6):1202–1207 (1993); Zabner et al., *Cell* 75(2):207–216 (1993); Li et al., *Hum. Gene Ther.* 4(4):403–409 (1993); Caillaud et al., *Eur. J. Neurosci.* 5(10):1287–1291 (1993); Vincent et al., *Nat. Genet.* 5(2):130–134 (1993); Jaffe et al., *Nat. Genet.* 1(5):372–378 (1992); and Levrero et al., *Gene* 101(2):195–202 (1991); and WO 93/07283; WO 93/06223; and WO 93/07282.

Gene delivery vectors of the present invention also include herpes vectors. Representative examples of such vectors include those disclosed by Kit in *Adv. Exp. Med. Biol.* 215:219–236 (1989); and those disclosed in U.S. Pat. No. 5,288,641 and EP 0176170 (Roizman). Additional exemplary herpes simplex virus vectors include HFEM/ICP6-LacZ disclosed in WO 95/04139 (Wistar Institute), pHSVlac described in Geller, *Science* 241:1667–1669 (1988), and in WO 90/09441 and WO 92/07945; HSV Us3::pgC-lacZ described in Fink, *Human Gene Therapy* 3:11–19 (1992); and HSV 7134, 2 RH 105 and GAL4 described in EP 0453242 (Breakefield), and those deposited with the ATCC as accession numbers ATCC VR-977 and ATCC VR-260.

Gene delivery vectors may also be generated from a wide variety of other viruses including, for example, poliovirus (Evans et al., *Nature* 339:385–388 (1989); and Sabin, *J. Biol. Standardization* 1:1 15–118 (1973)); rhinovirus; pox viruses, such as canary pox virus or vaccinia virus (Fisher-Hoch et al., *Proc. Natl. Acad. Sci. U.S.A.* 86:317–321 (1989); Flexner et al., *Ann. N.Y. Acad. Sci.* 569:86–103 (1989); Flexner et al., *Vaccine* 8:17–21 (1990); U.S. Pat. Nos. 4,603,112, 4,769,330 and 5,017,487; WO 89/01973); SV40 (Mulligan et al., *Nature* 277:108–114 (1979); influenza virus (Luytjes et al., *Cell* 59:1107–1113 (1989); McMicheal et al., *N. Eng. J. Med.* 309:13–17 (1983); and Yap et al., *Nature* 273:238–239 (1978)); HIV (Poznansky, *J. Virol.* 65:532–536 (1991)); measles (EP 0 440,219); astrovirus (Munroe et al., *J. Vir.* 67:3611–3614 (1993)); and coronavirus, as well as other viral systems (e.g., EP 0,440, 219; WO 92/06693; U.S. Pat. No. 5,166,057).

4. Non-viral Gene Delivery Vectors

Other gene delivery vectors and methods that may be employed for the expression of laminin5beta3 inhibitory antisense molecules such as, for example, nucleic acid expression vectors; polycationic condensed DNA linked or unlinked to killed adenovirus alone, for example, see Curiel, *Hum Gene Ther* 3:147–154 (1992); ligand linked DNA, for example, see Wu, *J Biol Chem* 264:16985–16987 (1989); eucaryotic cell delivery vectors; deposition of photopolymerized hydrogel materials; hand-held gene delivery particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip, *Mol Cell Biol* 14:2411–2418 (1994), and in Woffendin, *Proc. Natl. Acad. Sci.* 91:1581–1585 (1994).

Particle mediated gene delivery may be employed. Briefly, the laminin5beta3 inhibitory antisense molecule of interest can be inserted into conventional vectors that contain conventional control sequences for high level expression, and then be incubated with synthetic gene delivery molecules such as polymeric DNA-binding cations like polylysine, protamine, and albumin, linked to cell targeting ligands such as asialoorosomucoid, as described in Wu, et al., *J. Biol. Chem.* 262:4429–4432 (1987), insulin as described in Hucked, *Biochem Pharmacol* 40:253–263 (1990), galactose as described in Plank, *Bioconjugate Chem* 3:533–539 (1992), lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, PCT Patent Publication Nos. WO 95/13796, WO 94/23697, and WO 91/1laminin5beta345, and European Patent Publication No. 524,968. Nucleic acid sequences can be inserted into conventional vectors that contain conventional control sequences for high level expression, and then be incubated with synthetic gene delivery molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al., *Proc. NatL. Acad. Sci. U.S.A.* 91(24):11581–11585 (1994). Moreover, the coding sequence and the product of expression of such can be delivered through deposition of photopolymerized hydrogel materials.

Exemplary liposome and polycationic gene delivery vehicles are those described in U.S. Pat. Nos. 5,422,120 and 4,762,915, in PCT Patent Publication Nos. WO 95/13796, WO 94/23697, and WO 91/1laminin5beta35, in European Patent Publication No. 524,968 and in Starrier, *Biochemistry*, pp. 236–240 (1975) W. H. Freeman, San Francisco; Shokai, *Biochem. Biophys. Acta.* 600:1 (1980); Bayer, *Biochem. Biophys. Acta.* 550:464 (1979); Rivet, *Methods Enzymol.* 149:119 (1987); Wang, *Proc. Natl. Acad. Sci. U.S.A.* 84:7851 (1987); Plant, *Anal. Biochem.* 176:420 (1989).

EXAMPLES

The following experimental examples are offered by way of illustration, not limitation.

Example 1

Antisense Inhibition of Laminin5beta3 mRNA

A. Preparation of Transfection Mixture

For each transfection mixture, a carrier molecule, preferably a lipitoid or cholesteroid, was prepared to a working concentration of 0.5 mM in water, sonicated to yield a uniform solution, and filtered through a 0.45 μm PVDF membrane. The antisense or control oligonucleotide (SEQ ID NO:2–5) was prepared to a working concentration of 100 μM in sterile Millipore water.

The oligonucleotide was diluted in OptiMEM™ (Gibco/BRL), in a microfuge tube, to 2 μM, or approximately 20 μg oligo/ml of OptiMEM™. In a separate microfuge tube, lipitoid or cholesteroid, typically in the amount of about 1.5–2 nmol lipitoid/μg antisense oligonucleotide, was diluted into the same volume of OptiMEM™ used to dilute the oligonucleotide. The diluted antisense oligonucleotide was immediately added to the diluted lipitoid and mixed by pipetting up and down.

B. Transfection

SW620 cells and MDA231 cells were plated on tissue culture dishes one day in advance of transfection, in growth media with serum, to yield a density at transfection of 60–90%. The oligonucleotide/lipitoid mixture was added to the cells, immediately after mixing, to a final concentration of 100–300 nM antisense oligonucleotide. Cells were incubated with the transfection mixture at 37° C., 5% $CO_2$ for 4–24 hours. After incubation, the transfection mixture was removed and replaced with normal growth media with serum.

Total RNA was extracted using the RNeaSy™ kit (Quiagen Corporation, Chatsworth, Calif.), according to manufacturer's protocols.

C. Reverse Transcription

The level of target mRNA was quantitated using the Roche LightCycler™ real-time PCR machine. Values for the target mRNA were normalized versus an internal control (e.g., beta-actin).

For each 20 µl reaction, extracted RNA (generally 0.2–1 µg total) was placed into a sterile 0.5 or 1.5 ml microcentrifuge tube, and water was added to a total volume of 12.5 µl. To each tube was added 7.5 µl of a buffer/enzyme mixture, prepared by mixing (in the order listed) 2.5 µl $H_2O$, 2.0 µl 10× reaction buffer, 10 µl oligo dT (20 pmol), 1.0 µl dNTP mix (10 mM each), 0.5 µl RNAsin® (20u) (Ambion, Inc., Hialeah, Fla.), and 0.5 µl MMLV reverse transcriptase (50 u) (Ambion, Inc.). The contents were mixed by pipetting up and down, and the reaction mixture was incubated at 42° C. for 1 hour. The contents of each tube were centrifuged prior to amplification.

D. LightCycler™ Amplification of RT Reactions

An amplification mixture was prepared by mixing in the following order: 1× PCR buffer II, 3 mM $MgCl_2$, 140 µM each dNTP, 0.175 pmol each oligo, 1:50,000 dil of SYBR® Green, 0.25 mg/ml BSA, 1 unit Taq polymerase, and $H_2O$ to 20 µl. (PCR buffer II is available in 10× concentration from Perkin-Elmer, Norwalk, Conn.). In 1× concentration it contains 10 mM Tris pH 8.3 and 50 mM KCl. SYBR® Green (Molecular Probes, Eugene, Oreg.) is a dye which fluoresces when bound to double stranded DNA. As double stranded PCR product is produced during amplification, the fluorescence from SYBR® Green increases.

To each 20 µl aliquot of amplification mixture, 2 µl of template RT was added, and amplification was carried out according to standard protocols.

As shown in Table 1 below, laminin5beta3 message levels were decreased relative to actin message in MDA231 cells.

TABLE 1

Effect of Laminin5beta3 Oligonucleotides on Laminin5beta3 mRNA Levels in MDA231 Cells

| Antisense oligonucleotide | Laminin5beta3 message levels normalized to actin |
|---|---|
| No treatment | 0.90 |
| F31AS SEQ ID NO:2 | 0.06 |
| F31RC (control) SEQ ID NO:4 | 0.90 |
| F275AS SEQ ID NO:3 | 0.065 |
| F275RC (control) SEQ ID NO:5 | 0.64 |

Example 2

Cell Proliferation Assay

SW620 cells and MDA231 cells were seeded into 96 well plates at a density of 5000 cells per well. For a 4 day proliferation assay, 5 independent 96 well plates were prepared, one for each day. After overnight incubation, cells were transfected using the procedure described above. On each day of the proliferation assay, all medium was removed from one plate and frozen at −70° C. On day four, all plates were developed with the Quantos™ assay kit (Stratagene, La Jolla, Calif.) which determines the amount of DNA, and thus the number of cells, in each well. The results are shown in Tables 2 and 3 below.

As shown in Table 2, beginning at day 1, growth of wild type (untreated) cells continued to increase through day 4. In contrast, growth of cells treated with SEQ ID NO:2 did not increase over the 4 day period.

As shown in Table 3, beginning at day 1, growth of wild type (untreated) cells continued to increase through day 4. In contrast, growth of cells treated with SEQ ID NO:2 did not increase over the 4 day period.

TABLE 2

Effect of Laminin5beta3 Oligonucleotide F275 on Growth of SW620 Cells

| Oligonucleotide | Day 0 | Day 1 | Day 2 | Day 3 | Day 4 |
|---|---|---|---|---|---|
| Wild type (no oligo) | 750 | 1300 | 1700 | 3800 | 3900 |
| F275AS | 750 | 1200 | 700 | 650 | 600 |
| F275RC (control) | 750 | 1200 | 1300 | 2100 | 2800 |

TABLE 3

Effect of Laminin5beta3 Oligonucleotide F275 on Growth of MDA231 Cells

| Oligonucleotide | Day 0 | Day 1 | Day 2 | Day 3 | Day 4 |
|---|---|---|---|---|---|
| Wild type (no oligo) | 1250 | 2000 | 2300 | 2400 | 2700 |
| Wild type (no oligo) | 1250 | 2000 | 2400 | 2500 | 2800 |
| F275AS | 1400 | 1400 | 1100 | 1300 | 1200 |
| F275RC (control) | 1400 | 1600 | 1750 | 2400 | 2400 |

The oligonucleotides are:

CHIR3-3 275: CTTGCAGGTGGCATAGTAGAGCACG (SEQ ID NO:3)

CHIR3-4 31: CCGGTCCTTCAACTCAGCATACTTT (SEQ ID NO:2)

CHIR-3 275(RC): GCACGAGATGATACGGTGGACGTTC (SEQ ID NO:4)

CHIR-3 31(RC): TTTCATACGACTCAACTTCCTGGCC (SEQ ID NO:5)

Figure 3:
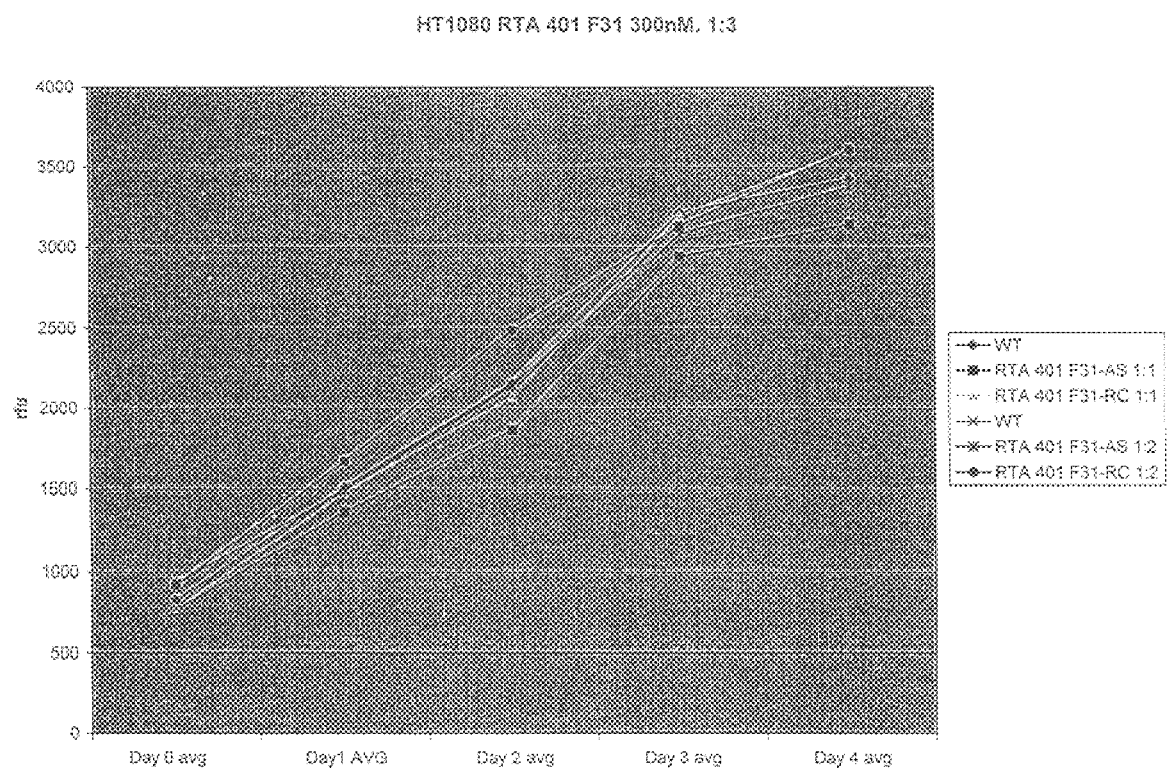
FIG. 3 illustrates that treatment of human fibrosarcoma cells HT1080 with antisense oligonucleotide SEQ ID NO:3 did not affect cell growth over a 4 day period.
Figure 4:
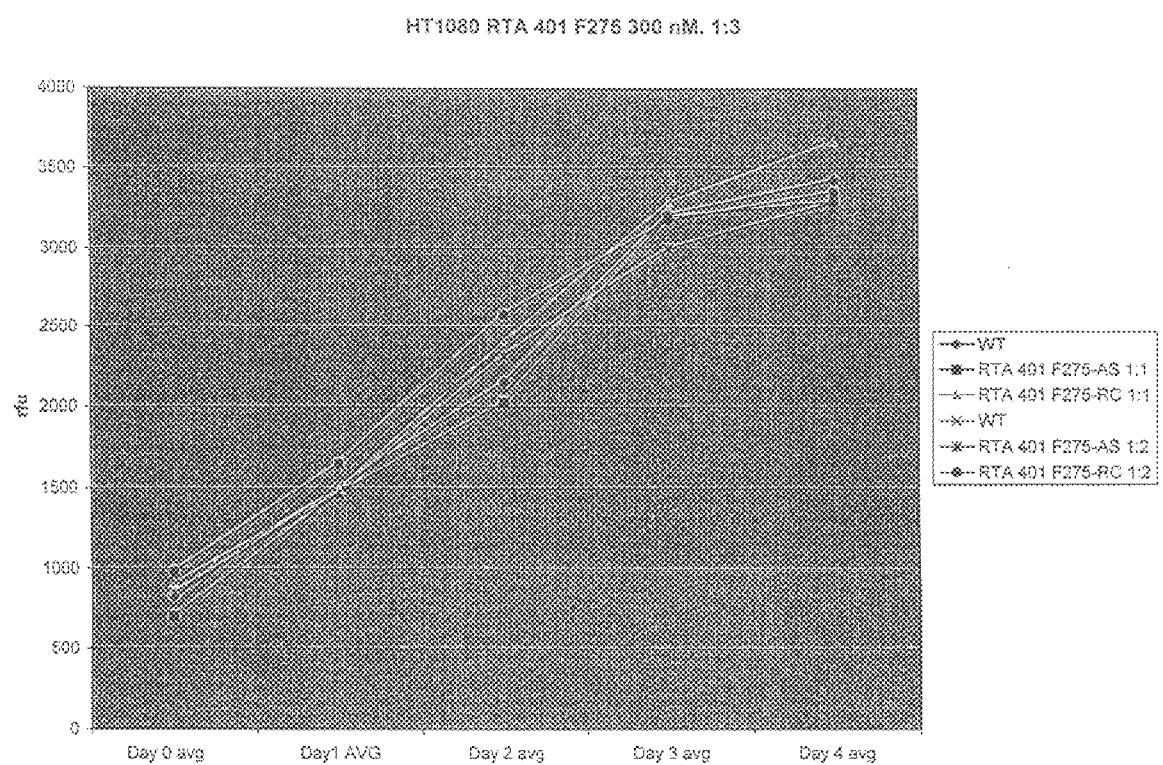
FIG. 4 illustrates that treatment of human fibrosarcoma cells HT1080 with antisense oligonucleotide SEQ ID NO:2 did not affect cell growth over a 4 day period.

As shown in FIG. 2, increasing the concentrations of antisense oligonucleotides SEQ ID NO:2 and 3 resulted in a dose-dependent decrease in proliferation of SW620 colon carcinoma cells. In contrast with the results using colon cancer cells, the antisense oligonucleotides did not have any significant effect on growth of human fibrosarcoma cells, as shown in FIGS. 3 and 4. FIGS. 3 and 4 show that over four days the growth of human fibrosarcoma cells HT1080 increased from just below 1000 pfu at day 0 to about 3400 pfu at day 4, and the growth rate did not vary significantly in the presence of antisense oligonucleotides SEQ ID NO:2 or 3, or reverse control oligonucleotides SEQ ID NO:4 or 5.

Thus, these results demonstrate the suitability of laminin5beta3 as a target for therapy of cancers of epithelial origin.

Example 3

Soft Agar Assay

Soft Agar Assay

The bottom layer consisted of 2 ml of 0.6% agar in media plated fresh within a few hours of layering on the cells. For the cell layer, cells transfected as described in Example 1 were removed from the plate in 0.05% trypsin and washed twice in media. Cells were counted in coulter counter, and resuspended to 106 per ml in media. 10 ml aliquots were placed with media in 96-well plates (to check counting with WST1), or diluted further for soft agar assay. 2000 cells were d in 800 ml 0.4% agar in duplicate wells above 0.6% agar bottom layer.

Media layer: After cell layer agar solidifies, 2 ml of media was bled on top and antisense or reverse control oligo was d without delivery vehicles. Fresh media and oligos are added every 3–4 days.

Colonies were formed in 10 days to 3 weeks. Fields of colonies were counted by eye. Wst-1 metabolism values were be used to compensate for small differences in starting cell number. Larger fields can be scanned for visual record of differences. SW620 cells transfected with antisense gave rise to fewer colonies compared to cells transfected with the control oligonucleotide.

Example 4

In Situ Hybridization

The specificity of laminin5beta3-based oligonucleotides probes for cancers of epithelial origin was demonstrated using labeled probes capable of specifically binding to SEQ ID NO: 1. A series of in situ hybridization experiments showed that the probe bound to prostate cancer tissue, but not normal prostate tissue. The probe bound to all colon cancer tissue samples but to a lesser extent in normal colon tissue. The probe bound to breast cancer tissue samples but not to normal breast tissue, and light staining was seen when probe was hybridized to breast tissue showing hyperplasia. A greater degree of hybridization of the probe was seen in lung cancer tissue than in normal lung tissue.

From the foregoing it will be appreciated that, although specific embodiments of the invention have been described herein for purposes of illustration, various modifications may be made without departing from the spirit and scope of the invention. Accordingly, the invention is not limited except as by the appended claims. All patents and publications discussed herein are incorporated by reference herein in their entirety.

What is claimed is:

1. An isolated laminin5beta3 inhibitor comprising an antisense molecule, the antisense molecule comprising a nucleic acid sequence selected from the group consisting of SEQ ID NO:2 and 3.

2. A composition, comprising a therapeutically effective amount of a laminin5beta3 inhibitor in a pharmaceutically acceptable carrier, wherein the laminin5beta3 inhibitor is an antisense molecule and comprises a nucleic acid sequence selected from the group consisting of SEQ ID NO: 2 and 3.

3. The composition of claim 2, comprising two or more laminin5beta3 inhibitors.

4. A method of decreasing the expression of laminin5beta3 in a mammalian cell, comprising administering to said cell an antisense molecule, wherein said antisense molecule comprises a nucleic acid sequence selected from the group consisting of SEQ ID NO:2 and 3.

5. A diagnostic kit for detecting the presence of a tumor cell of epithelial origin in a biological sample, said kit comprising at least one oligonucleotide selected from the group consisting of SEQ ID NOs:2 and 3, and at least one control oligonucleotide that does not hybridize with a polynucleotide of SEQ ID NO:1 under stringent conditions.

6. The kit of claim 5 comprising oligonucleotides of SEQ ID NO:2 and 3.

7. The kit of claim 5 wherein said tumor cell is of colon origin.

8. The kit of claim 5 wherein said tumor cell is of prostate origin.

9. An antisense oligonucleotide that inhibits the expression of laminin5beta3 encoded by SEQ ID NO:1 wherein said antisense oligionucleotide hybridizes to said SEQ ID NO: 1.

* * * * *

SEQUENCE LISTING

```
<160> NUMBER OF SEQ ID NOS: 5

<210> SEQ ID NO 1
<211> LENGTH: 3971
<212> TYPE: DNA
<213> ORGANISM: Homo sapiens

<400> SEQUENCE: 1
gctttcaggc gatctggaga aagaacggca gaacacacag caaggaaagg tcctttctgg      60
ggatcacccc attggctgaa gatgagacca ttcttcctct tgtgttttgc cctgcctggc     120
ctcctgcatg cccaacaagc ctgctcccgt ggggcctgct atccacctgt tggggacctg     180
cttgttggga ggacccggtt tctccgagct tcatctacct gtggactgac caagcctgag     240
acctactgca cccagtatgg cgagtggcag atgaaatgct gcaagtgtga ctccaggcag     300
cctcacaact actacagtca ccgagtagag aatgtggctt catcctccgg ccccatgcgc     360
tggtggcagt cccagaatga tgtgaaccct gtctctctgc agctggacct ggacaggaga     420
ttccagcttc aagaagtcat gatggagttc cagggcccca tgcccgccgg catgctgatt     480
gagcgctcct cagacttcgg taagacctgg cgagtgtacc agtacctggc tgccgactgc     540
acctccacct tccctcgggt ccgccagggt cggcctcaga gctggcagga tgttcggtgc     600
cagtccctgc ctcagaggcc taatgcacgc ctaaatgggg ggaaggtcca acttaacctt     660
atggatttag tgtctgggat tccagcaact caaagtcaaa aaattcaaga ggtgggggag     720
atcacaaact tgagagtcaa tttcaccagg ctggccctg tgcccaaag gggctaccac     780 cctcccagcg cctactatgc tgtgtcccag ctccgtctgc aggggagctg cttctgtcac     840
```

-continued

```
ggccatgctg atcgctgcgc acccaagcct ggggcctctg caggcccctc caccgctgtg      900
caggtccacg atgtctgtgt ctgccagcac aacactgccg gcccaaattg tgagcgctgt      960
gcacccttct acaacaaccg gccctggaga ccggcggagg gccaggacgc ccatgaatgc     1020
caaaggtgcg actgcaatgg gcactcagag acatgtcact ttgacccgc tgtgttttgcc     1080
gccagccagg gggcatatgg aggtgtgtgt gacaattgcc gggaccacac cgaaggcaag     1140
aactgtgagc ggtgtcagct gcactatttc cggaaccggc gcccgggagc ttccattcag     1200
gagacctgca tctcctgcga gtgtgatccg gatggggcag tgccagggc tccctgtgac      1260
ccagtgaccg ggcagtgtgt gtgcaaggag catgtgcagg gagagcgctg tgacctatgc     1320
aagccgggct tcactggact cacctacgcc aacccgcagg gctgccaccg ctgtgactgc     1380
aacatcctgg ggtcccggag ggacatgccg tgtgacgagg agagtgggcg ctgcctttgt     1440
ctgcccaacg tggtgggtcc caaatgtgac cagtgtgctc cctaccactg gaagctggcc     1500
agtggccagg gctgtgaacc gtgtgcctgc gacccgcaca actcccctca gcccacagtg     1560
caaccagttc acagggcagt gccctgtcgg gaaggctttg gtggcctgat gtgcagcgct     1620
gcagccatcc gccagtgtcc agaccggacc tatggagacg tggccacagg atgccgagcc     1680
tgtgactgtg atttccgggg aacagagggc ccgggctgcg acaaggcatc aggccgctgc     1740
ctctgccgcc ctggcttgac cgggccccgc tgtgaccagt gccagcgagg ctactgcaat     1800
cgctaccccg tgtgcgtggc ctgccaccct tgcttccaga cctatgatgc ggacctccgg     1860
gagcaggccc tgcgctttgg tagactccgc aatgccaccg ccagcctgtg gtcagggcct     1920
gggctggagg accgtggcct ggcctcccgg atcctagatg caaagagtaa gattgagcag     1980
atccgagcag ttctcagcag ccccgcagtc acagagcagg aggtggctca ggtggccagt     2040
gccatcctct ccctcaggcg aactctccag ggcctgcagc tggatctgcc cctgaggag      2100
gagacgttgt cccttccgag agacctggag agtcttgaca gaagcttcaa tggtctcctt     2160
actatgtatc agaggaagag ggagcagttt gaaaaaataa gcagtgctga tccttcagga     2220
gccttccgga tgctgagcac agcctacgag cagtcagccc aggctgctca gcaggtctcc     2280
gacagctcgc gccttttgga ccagctcagg gacagccgga gagaggcaga gaggctggtg     2340
cggcaggcgg gaggaggagg aggcaccggc agccccaagc ttgtggccct gaggctggag     2400
atgtcttcgt tgcctgacct gacacccacc ttcaacaagc tctgtggcaa ctccaggcag     2460
atggcttgca ccccaatatc atgccctggt gagctatgtc cccaagacaa tggcacagcc     2520
tgtggctccc gctgcagggg tgtccttccc agggccggtg gggccttctt gatgcggggg     2580
caggtggctg agcagctgcg gggcttcaat gcccagctcc agcggaccag gcagatgatt     2640
agggcagccg aggaatctgc ctcacagatt caatccagtg cccagcgctt ggagacccag     2700
gtgagcgcca gccgctccca gatggaggaa gatgtcagac gcacacggct cctaatccag     2760
caggtccggg acttcctaac agaccccgac actgatgcag ccactatcca ggaggtcagc     2820
gaggccgtgc tggccctgtg gctgcccaca gactcagcta ctgttctgca aagatgaat      2880
gagatccagg ccattgcagc caggctcccc aacgtggact tggtgctgtc ccagaccaag     2940
caggacattg cgcgtgcccg ccggttcag gctgaggctg aggaagccag gagccgagcc      3000
catgcagtgg agggccaggt ggaagatgtg gttgggaacc tgcggcaggg gacagtggca     3060
ctgcaggaag ctcaggacac catgcaaggc accagccgct cccttcggct tatccaggac     3120
agggttgctg aggttcagca ggtactgcgg ccagcagaaa agctggtgac aagcatgacc     3180
```

```
aagcagctgg gtgacttctg gacacggatg gaggagctcc gccaccaagc ccggcagcag      3240
ggggcagagg cagtccaggc ccagcagctt gcggaaggtg ccagcgagca ggcattgagt      3300
gcccaagagg gatttgagag aataaaacaa aagtatgctg agttgaagga ccggttgggt      3360
cagagttcca tgctgggtga gcagggtgcc cggatccaga gtgtgaagac agaggcagag      3420
gagctgtttg gggagaccat ggagatgatg gacaggatga agacatgga gttggagctg      3480 ctgcggggca gccaggccat catgctgcgc tcggcggacc tgacaggact ggagaagcgt      3540
gtggagcaga tccgtgacca catcaatggg cgcgtgctct actatgccac ctgcaagtga      3600
tgctacagct tccagcccgt tgccccactc atctgccgcc tttgcttttg gttggggggca     3660 gattgggttg gaatgctttc catctccagg agactttcat gcagcctaaa gtacagcctg      3720
gaccacccct ggtgtgtagc tagtaagatt accctgagct gcagctgagc ctgagccaat      3780
gggacagtta cacttgacag acaaagatgg tggagattgg catgccattg aaactaagag      3840
ctctcaagtc aaggaagctg ggctgggcag tatcccccgc ctttagttct ccactgggga      3900
ggaatcctgg accaagcaca aaacttaac aaaagtgatg taaaaatgaa aagccaaata      3960
aaaatctttg g                                                          3971

<210> SEQ ID NO 2
<211> LENGTH: 25
<212> TYPE: DNA
<213> ORGANISM: Artificial Sequence
<220> FEATURE:
<223> OTHER INFORMATION: Polynucleotide sequences of the antisense
      laminin5beta3 oligonucleotides.

<400> SEQUENCE: 2
ccggtccttc aactcagcat acttt                                            25

<210> SEQ ID NO 3
<211> LENGTH: 25
<212> TYPE: DNA
<213> ORGANISM: Artificial Sequence
<220> FEATURE:
<223> OTHER INFORMATION: Polynucleotide sequences of the antisense
      laminin5beta3 oligonucleotides.

<400> SEQUENCE: 3
cttgcaggtg gcatagtaga gcacg                                            25

<210> SEQ ID NO 4
<211> LENGTH: 25
<212> TYPE: DNA
<213> ORGANISM: Artificial Sequence
<220> FEATURE:
<223> OTHER INFORMATION: Control oligonucleotide

<400> SEQUENCE: 4
gcacgagatg atacggtgga cgttc                                            25

<210> SEQ ID NO 5
<211> LENGTH: 25
<212> TYPE: DNA
<213> ORGANISM: Artificial Sequence
<220> FEATURE:
<223> OTHER INFORMATION: Control oligonucleotide

<400> SEQUENCE: 5
tttcatacga ctcaacttcc tggcc                                            25
```